United States Patent [19]  
Virta et al.

[11] Patent Number: 4,783,793  
[45] Date of Patent: Nov. 8, 1988

[54] X-RAY APPARATUS FOR PANORAMIC TOMOGRAPHY INCLUDING CONTROL SYSTEM

[75] Inventors: Arto Virta, Vantaa; Pekka Strömmer, Espoo, both of Finland

[73] Assignee: Planmeca Oy, Finland

[21] Appl. No.: 905,178

[22] Filed: Sep. 9, 1986

Related U.S. Application Data

[63] Continuation-in-part of Ser. No. 868,724, May 30, 1986.

[30] Foreign Application Priority Data

Sep. 13, 1985 [FI] Finland ............................ 853524

[51] Int. Cl.⁴ .............................................. A61B 6/14
[52] U.S. Cl. ...................................... 378/39; 378/40; 378/38
[58] Field of Search ................... 378/38, 39, 40, 15, 378/147, 148, 150

[56] References Cited

U.S. PATENT DOCUMENTS 4,242,585 12/1980 Yamano .................................. 378/39
4,286,162  8/1981 Suzuki .................................... 378/40
4,418,419 11/1983 Schreiber et al. .................... 378/040
4,475,224 10/1984 Grassme ................................. 378/38
4,521,899  6/1985 Finkenzeller et al. ................ 378/40
4,606,063  8/1986 Berghagen ........................... 378/148

Primary Examiner—Carolyn E. Fields  
Assistant Examiner—David P. Porta  
Attorney, Agent, or Firm—Steinberg & Raskin

[57] ABSTRACT

Panoramic tomography X-ray apparatus such as for obtaining images of dental systems, comprises a rotatably mounted arm to which the X-ray tube of an X-ray generator and an X-ray film cartridge, along with film transport equipment, are mounted, and a control system for controlling the functioning of the equipment of the apparatus on the basis of control data and a program pre-stored therein. A control system controls the speed of a rotary motion motor that rotates the arm, the speed of the film transport motor and the distribution of those speeds, independently of each other. In this manner, it is possible to photograph dental systems of varying sizes and shapes both sharply and with suitable exposure time. In addition to controlling the speeds of the rotary motion and film transport motors, the control system may also control the anode current and/or the anode voltage of the X-ray generator during the exposure sequence.

24 Claims, 7 Drawing Sheets

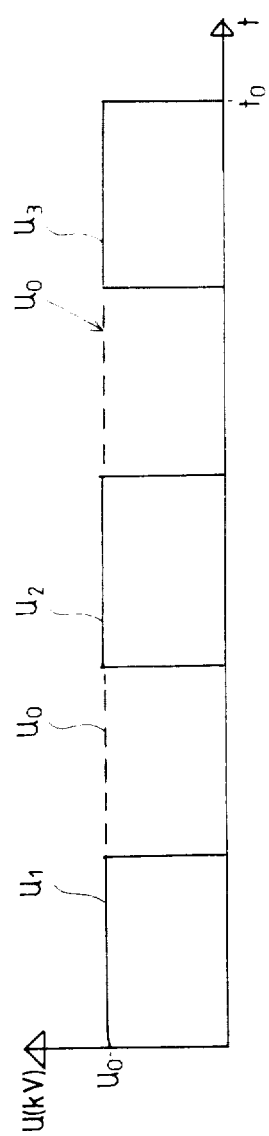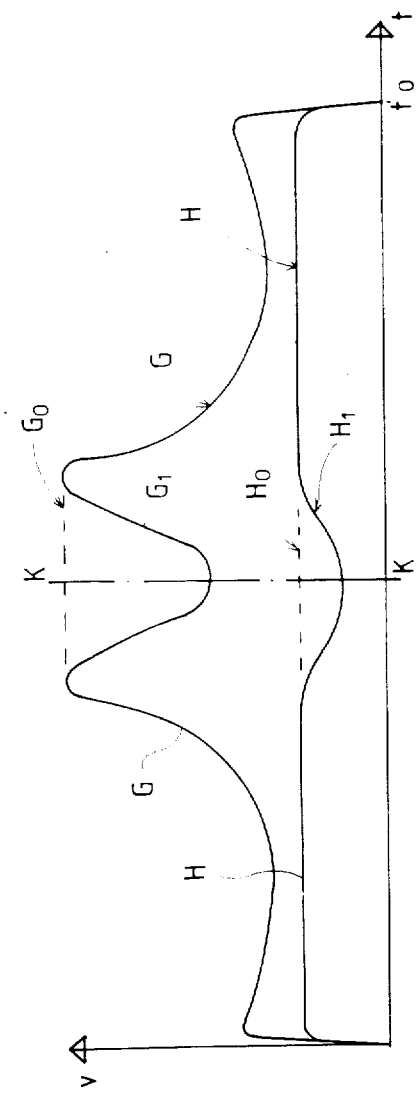

X-RAY APPARATUS FOR PANORAMIC TOMOGRAPHY INCLUDING CONTROL SYSTEM

BACKGROUND OF THE INVENTION

This is a continuation-in-part of application Ser. No. 868,724 filed May 30, 1986, now Pat. No. 4,741,007.

The present invention relates generally to X-ray apparatus for panoramic tomography and, more particularly, to X-ray apparatus for panoramic tomography which includes a control system for controlling the functioning of components of the apparatus, such as the transport of the X-ray film and the rotation of the arm to which the tube head of the X-ray generator and the cartridge containing X-ray film with the film transport equipment are fastened.

The design and principles of operation of most panoramic X-ray apparatus used for dental photography provide for rotation of an X-ray beam around the patient's head in a manner such that the dental arch will be photographed in the form of a flat image on moving film.

In order to obtain a sharp picture of the object being photographed and to eliminate images of objects which may be located in front of or to the rear of the object being photographed by "fogging" the unwanted images from focus, the transverse velocity of the X-ray film relative to the X-ray beam must be equal to the sweep velocity of the ray beam multiplied by the magnification ratio. The magnification ratio is determined by the ratio of the distance between the point of focus of the X-ray tube and the film to the distance between the point of focus and the object being photographed.

The thickness of the layer being photographed in panoramic tomography is directly proportional to the distance of the instantaneous center of rotation from the plane of the X-ray film, and inversely proportional to the magnification and to the width of the ray beam. Important factors to be considered as to how the object being photographed will be presented is how the point of focus, the object being photographed, and the film plane are located with respect to each other. The instantaneous center of rotation is significant with respect to the sweep velocity.

Based upon the foregoing, it is possible to represent a situation in the form of a basic equation of panoramic photography:

$$v_1/v_0 = L_1/L_0,$$

$v_0 = \omega r$, where $L_0$ = the distance from the focus F to the point being photographed at a given moment $L_1$ = the distance from the focus F to the film plane $\omega$ = the angular velocity of the rotary movement around the center of rotation $r$ = the distance of the point being photographed from the instantaneous center of rotation $v_1$ = the velocity of an image point on the picture plane or the film plane In order to obtain the orthogonal fluoroscopic image of the teeth and jaw, typical to panoramic tomography X-ray equipment, a narrow X-ray beam is generated which penetrates through the patient. The anode current and anode voltage of the tube producing the X-ray beam must be controlled according to patient characteristics while the X-ray beam is rotated around the patient along a path such that the X-ray beam intersects the jaw and the teeth as perpendicular to them as possible. The film within its film cartridge is located on the opposite side of the patient with respect to the X-ray tube and must be moved at such a speed that a sharp image of the desired layer of the patient's chin-bone and dental system are obtained the film.

In early apparatus of this type, the anode voltage and anode current, which remain constant during the entire exposure sequence, are manually set at the X-ray generator. A single motor functions to both rotate the system components as well as to provide transport of the X-ray film in the cartridge. The dual function of the single motor is obtained using a fixed transmission and the layer for which a sharp scan is obtained is defined by the gear ratio of the mechanism that transmits the motion of the motor to the film cartridge.

More recently, X-ray tomography apparatus had been proposed which include a separate motor for moving the film cartridge. Usually, this motor comprises a constant-speed motor. The gear ratio of the film cartridge is mechanically changed based upon the rotary movement.

A drawback of these conventional control systems which are based on mechanically interrelated motion speeds is that the ratio of the motion speeds is mechanically fixed and cannot be changed in different stages of an exposure sequence. Therefore, only a single type jaw profile can be photographed with desired sharpness using such conventional devices. However, as known, human jaws vary to a great extent and therefore it is necessary to compromise in the use of these conventional devices. In this connection, the conventional devices are designed to provide sharp photographs of a so-called average jaw profile so that jaws which differ somewhat from the standard will be photographed at least satisfactorily.

In order to eliminate these drawbacks, recent tomography apparatus are provided with a separate film cartridge transport motor whose speed can be varied both as previously, i.e., with control being provided by the rotary motion, as well as independently of the rotary motion so that the layer being photographed can be changed within certain limits to enable good panoramic photographs to be obtained for different shapes of jaws.

In these more recent apparatus in which the rotary motion and the film cartridge movement are obtained by separate motors, the rotary motion motor is generally a constant speed motor. Therefore, it has been possible to change the layer which is being sharply photographed only by changing the speed of the film cartridge movement. However, this procedure necessarily requires that the exposure time be changed directly proportionally to the film cartridge transport speed. This results in the picture being unevenly exposed having lighter and darker spots depending on whether the newly focused image is in front of or behind the basic sharply focused image determined the mechanical system. Similarly, in conventional systems provided with two separate motors, it has not been possible to make necessary corrections to compensate for the absorption of radiation in the region of the cervical spine since at least one of the motors is always of the constant-speed type. Therefore, it has been necessary to compensate for radiation absorption by changing the intensity of the X-ray beam. However, since regulation on the order of milli-amperes with which the intensity is controlled is quite slow due to the properties of the glow filament of the X-ray tube, it is necessary to change the intensity by changing the anode voltage of the X-ray tube. Thus, depending on the properties of the patient and the particular amplification apparatus which is used, the maximum contrast is achieved with a particular anode voltage and deviation from this voltage results in less favorable contrast. These problems exist today in conventional panoramic tomography apparatus.

SUMMARY OF THE INVENTION

It is an object of the present invention to provide new and improved panoramic tomography X-ray apparatus including a control system for controlling various components of the apparatus to overcome the drawbacks of conventional arrangements discussed above.

Briefly, in accordance with the present invention, this as well as other objects are attained by providing panoramic tomography X-ray apparaus including a rotatably mounted arm, an X-ray tube of an X-ray generator and a cartridge containing X-ray film being mounted on the arm for rotation therewith, a rotary motion motor for rotating the arm and a film transport motor for transporting the X-ray film, and control system means for controlling the speed of the rotary motion motor of the arm, the speed of the film transport motor, and the distribution or variation of these speeds during an exposure sequence independently of each other as a function of control data and a program pre-stored in the control system means so that dental systems of varying sizes and shapes can be photographed by the panoramic tomography X-ray apparatus both sharply and within a suitable exposure time.

In accordance with the invention, the speeds of both the rotary motion and the film cartridge transport motor can be adjusted separately and independently. Additionally, the control system also functions to control the voltage and current of the X-ray tube during exposure, preferably in a continuous manner. It is also possible to provide an automatic primary blind for adjusting the shape of a radiation beam generated by the X-ray tube and to control the primary blind means by the same control system. The control system means of the present invention may also be pre-programed to cause the X-ray apparatus to photograph only small areas of a patient, such as regions of the salivary glands and maxillary sinuses.

DESCRIPTION OF THE DRAWINGS

A more complete appreciation of the present invention and many of the attendant advantages thereof will be readily understood by reference to the following detailed description when considered in connection with the accompanying drawings in which:

FIG. 6 is a graphical illustration showing examples of advantageous speed distributions between the rotary motion motor and the film transport motor during the exposure sequence;

FIG. 7 is a graphical illustration showing control of the anode voltage of the X-ray tube obtained using X-ray apparatus in accordance with the invention;

DESCRIPTION OF THE PREFERRED EMBODIMENTS

Figure 1:
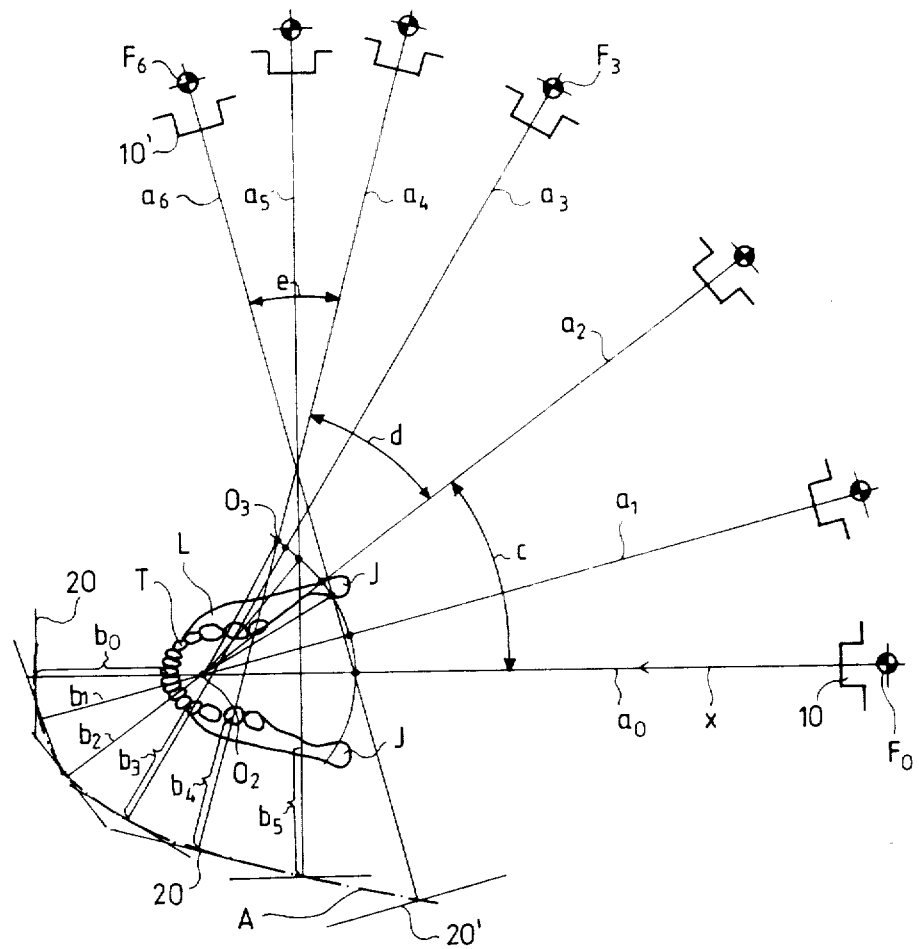
FIG. 1 is a schematic drawing illustrating an exposure sequence of panoramic tomography X-ray apparatus which can be obatined in accordance with the present invention.

Referring now to the drawings wherein like reference characters designate identical or corresponding parts throughout the several views and, more particularly, to FIG. 1, the geometry of panoramic tomography X-ray apparatus provided with a control system in accordance with the invention is illustrated. An X-ray tube is designated 10 and is shown in seven different positions which are assumed during the exposure sequence, the point of focus of the X-ray tube 10 being designated $F_0$ to $F_6$. The X-ray tube 10 generates an X-ray beam X which is directed to through the teeth T and jaw bone L onto a film 20 along line a. Thus, in FIG. 1, the X-ray beam X is shown in seven different positions $a_0$ to $a_6$. In its last or end position, the X-ray tube is designated 10', the film is designated 20' and the point of focus of X-ray tube 10 is designated $F_6$. The joints of jaw bone L are designated J.

Figure 2:
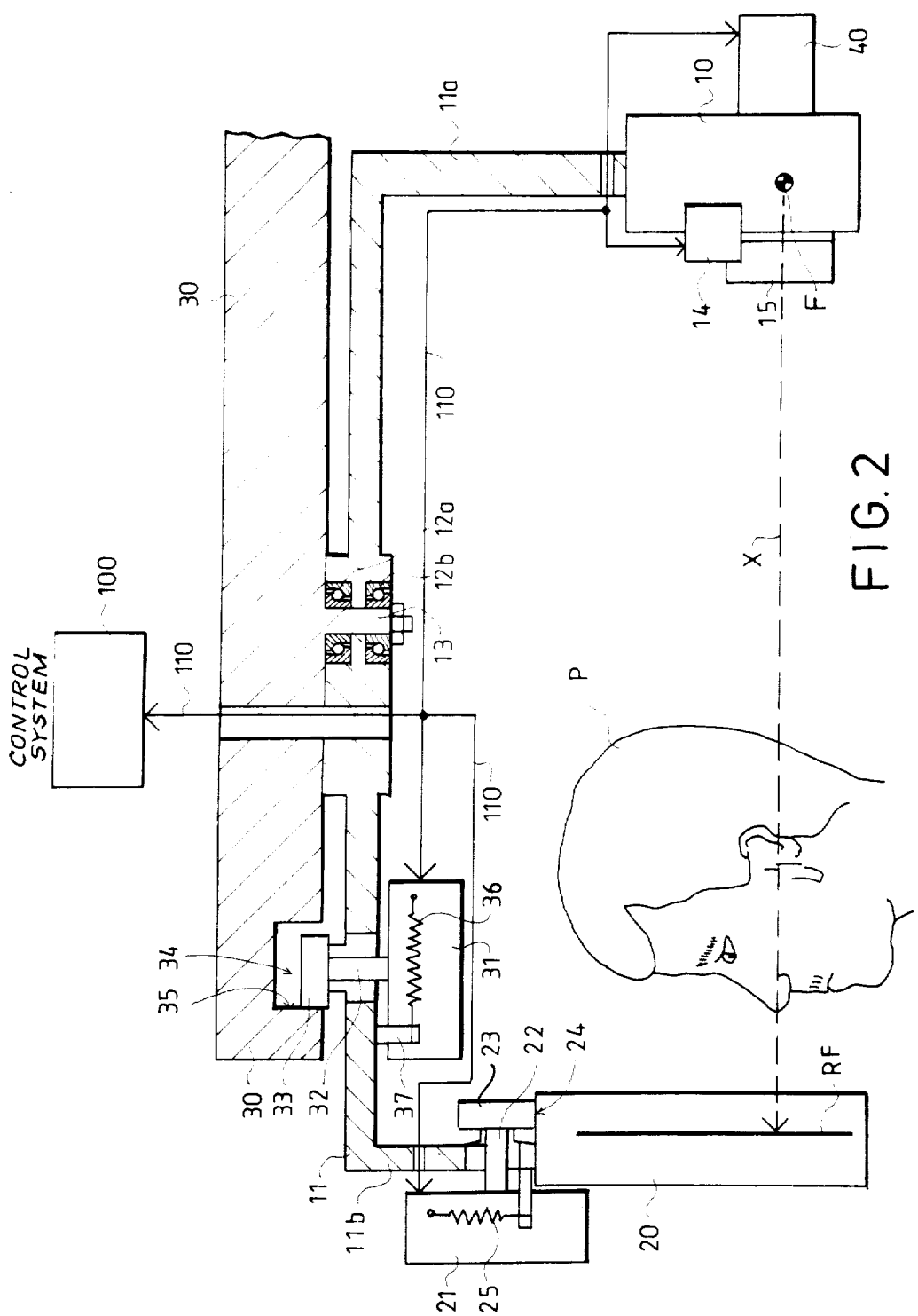
FIG. 2 is a central vertical sectional view of apparatus in accordance with the present invention during use.

Referring to FIGS. 1 and 2, in the frontal area of the dental arch comprising the space defined between X-ray $a_0$ and $a_2$ and designated sector c, a rotatable arm 11 which carries the X-ray tube 10 on one of its ends and the film cartridge 20 on the other one of its ends rotates in a horizontal plane around a vertical axis $O_2$. In the portion of the exposure sequence between X-rays $a_2$ and $a_4$, designated sector d, the axis of rotation smoothly moves along a curved path to the vertical axis $O_3$ and, subsequently, the vertical axis continuous to move away from the center of rotation $O_2$. When the apparatus operates in accordance with the geometry illustrated in FIG. 1, the orthogonality of the obtained image is sharp and accurate both in the frontal area of the dental arch as well as in the side areas and in the rear region of the jaw bone L up to joints J. Magnification will also be constant over the entire image field as can be seen from the fact that the distances $b_0$ to $b_5$ of the film from the layer being photographed is essentially constant over the entire exposure sequence. Since the distances $b_0$ to $b_5$ is substantiallY constant, the X-ray film 20 can be brought closer to a patient P (FIG. 2) in order to reduce the magification ratio without risking hitting the patient with the film cartridge.

Referring now to FIG. 2, connection of the X-ray tube 10 and the film cartridge 20 to the rotatable arm 11 for rotation in a horizontal plane around axis 13 as well as around other axis of rotation situated proximate to axis 13 in accordance with the principles described in connection with FIG. 1 is illustrated. The details of the mechanism illustrated in FIG. 2 are described in applicant's co-pending U.S. application Ser. No. 868,724 filed May 30, 1986. The control system forming a part of the invention finds advantageous use in connection with such a mechanism although it will be understood that the invention is not restricted to the use of a control system with this particular mechanism.

Briefly, the apparatus comprises a frame 30 whose position can be vertically adjusted to a suitable working height on a base structure. A rotatable arm 11 is suspended from frame 30 by means of a mechanism described in the above-mentioned application Ser. No. 868,724. The X-ray tube 10 is mounted on one end of arm 11 supported by a vertical part 11a. A film cartridge 20 containing X-ray film RF is mounted at the other end of arm 11 supported by a vertical part 11b. The film transport mechanism and other devices are mounted on arm 11 in accordance with the invention. The rotating arm 11 is suspended from frame 30 by means of bearings 12a and 12b so as to be rotatable about a vertical axis defined by shaft 13. The vertical shaft 13 is not fixed but rotates in a horizontal plane with respect to the fixed frame 30 during the exposure sequence.

Arm 11 is rotated around the vertical shaft 13 by means of a rotary motion motor 31 whose output shaft has a drive wheel 33 fastened to its end. The drive wheel 33 is urged against a vertical side 35 of a drive groove 34 by means of a spring 36 fastened to a pin 37. The shape of the groove 34 is substantially similar to the shape of the jaw bone and the dental arch as described in detail in the above-mentioned application Ser. No. 868,724. The film cartridge is moved in the direction of the film plane by means of a film transport motor 21 having a shaft 22 to the end of which a drive wheel 23 is connected which is urged against a flat top side 24 of the film cartridge 20 by means of a compression spring 25. Rotary motion and film transport motors 21 and 31 may suitably comprise stepping motors or synchronous motors which are controlled by the control system 100 in accordance with the invention. The control system 100 also controls a drive motor 14 of the primary blind 15 and the X-ray generator 40 is described in greater detail below.

The relationship between a control system and the other components of X-ray apparatus for panoramic tomography in accordance with an embodiment of the invention is illustrated in FIG. 2. During the exposure, the X-ray beam X is directed to the patient P from the point of focus F of the X-ray tube head 10. After passing through the patient the X-ray beam falls on the film RF in cartridge 20 creating a latent picture of the patient P on the film. During exposure, the tube head 10 and film cartridge 20 rotate around the patient following a motion path determined by the mechanism described above. Generally, the motor 31 rotates the arm 11 which support the tube head 10 and the film cartridge 20 at a speed determined by the control system, designated 100. At the same time, the film RF in cartridge 20 is transported by motor 21 at a speed determined by the control system 100. As discussed below, the control system 100 has a keyboard and a display for entering and monitoring control instructions as well as the control electronics required by motors 21 and 31 and tube head 10 as described below. The control system 100 is connected to the peripheral components of the X-ray apparatus by cable 110.

Figure 3:
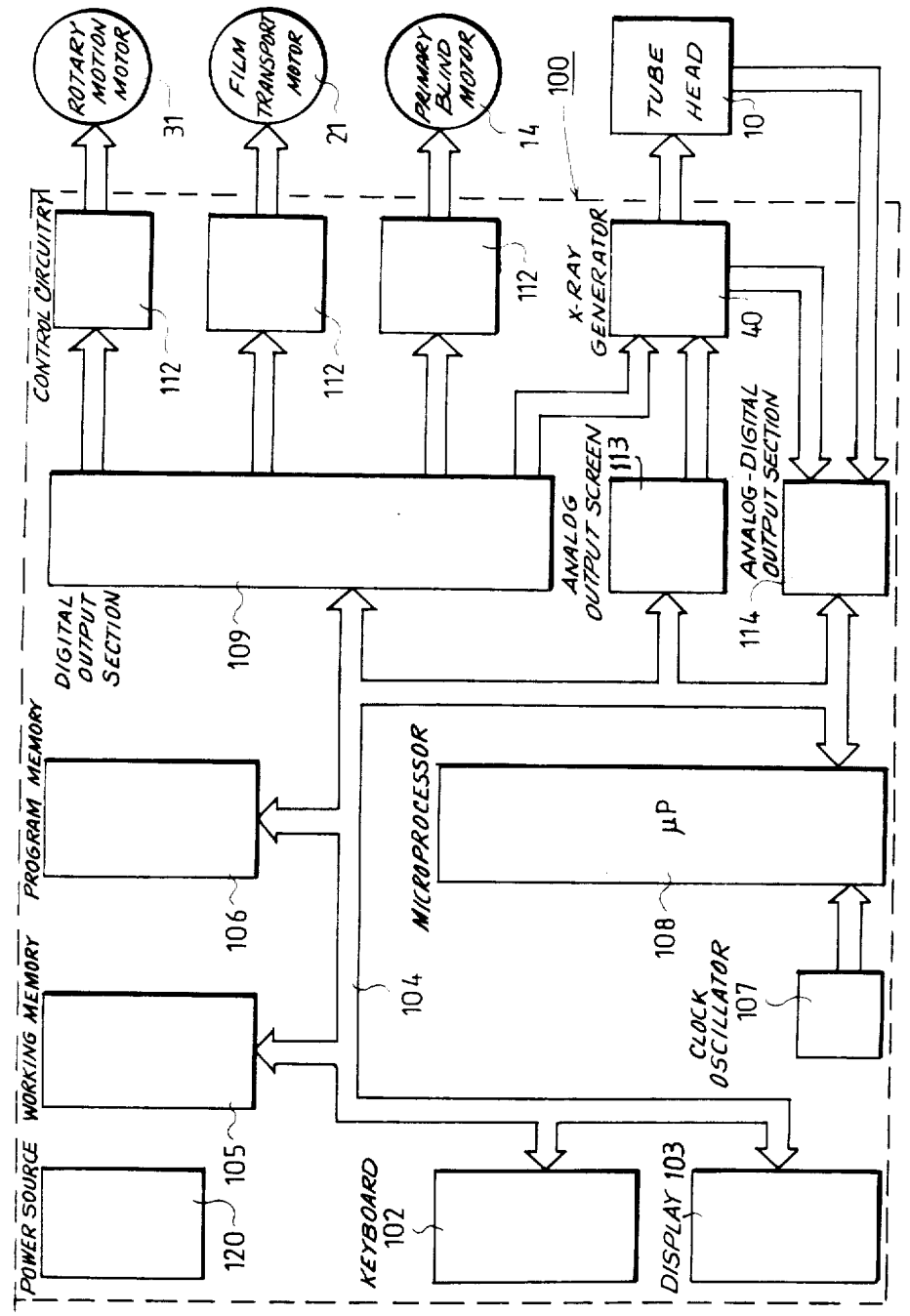
FIG. 3 is a block diagram of a control system for use in X-ray apparatus in accordance with the invention.

Referring to FIG. 3, one embodiment of a control system in accordance with the invention is illustrated in block form. The functions of the X-ray apparatus are controlled by a microprocessor 108 synchronized by a clock oscillator 107. The microprocessor 108 inherently includes a working memory 105 and a program memory 106. Control information is input into the control system by means of a keyboard 102 and the control system is monitored at display 103.

A digital output section 109 is coupled to the microprocessor 108 through bus 104. The digital output section 109 is in turn coupled to the rotary motion and film transport motors 31 and 21 through appropriate electronic control systems 112 so that the microprocessor controls the direction and speed of rotation of the rotary motion motor 31 and the film transport motor 21. The microprocessor is also coupled to the motor 14 of the primary blind 15 through bus 104, digital output section 109 and control circuitry 112. Furthermore, microprocessor 108 controls the X-ray generator 40 through both of the digital outpt section 109 as well as an analog output section 113. The X-ray generator 40 supplies power to the X-ray tube head 10. Information as to the status of the X-ray generator 40 as well as the tube head 10 is input to the working memory of the microprocessor 108 through an analog/digital input section 114. The various components of the control system 100 are powered by a power source 120.

Figure 4:
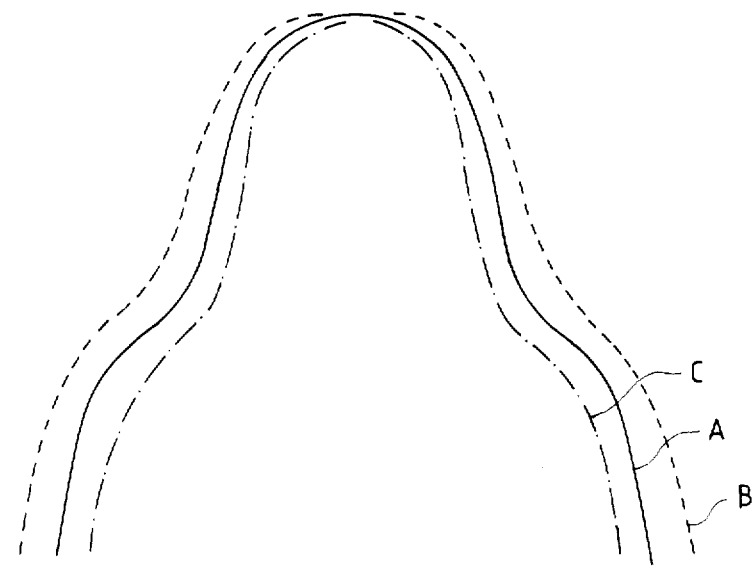
FIG. 4 is a diagrammatic drawing illustrating examples of dental arches of different sizes which can be sharply photographed using apparatus in accordance with the invention.

An important advantage of apparatus in accordance with the invention is that sharp photographs can be obtained of jaws of different sizes. Referring to FIG. 4, profile A illustrates an average jaw size for which the mechanism of the apparatus is designed for example, the drive groove 34 has a configuration which corresponds to the jaw profile A. The speed of the rotary motion motor 31 which rotates arm 11 and the transport motor 21 for moving the film cartridge 20 are stored in the control system 100 for each point of the profile A with which the actual layer of the jaw being photographed precisely corresponds. However, in accordance with an important feature of the control system of the invention, the speeds of the rotary motion motor 31 and film transport motor 21 can be changed as desired using the keyboard 102 so that, for example, a jaw structure which is larger than average (profile B) or smaller than average (profile C), such as a child's jaw, can be sharply photographed using a constant exposure time.

Figure 5:
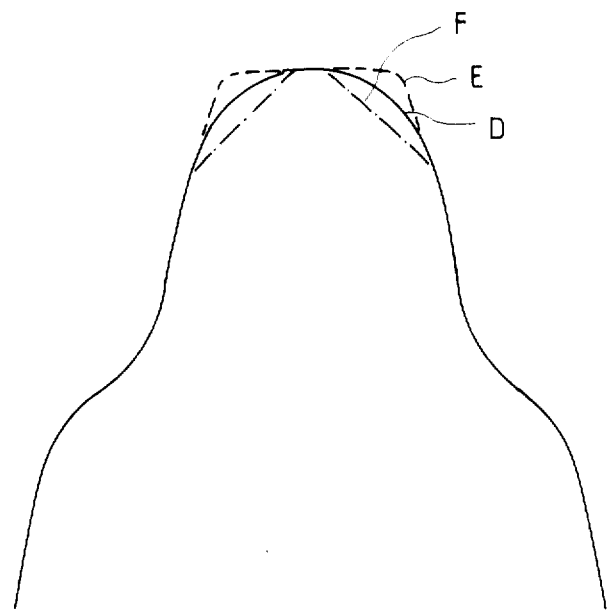
FIG. 5 is a diagrammatic illustration similar to FIG. 4 illustrating examples of dental arches of varying shapes which can be sharply photographed using apparatus in accordance with the invention.

The present invention also permits sharp photographs to be taken of jaws whose shape vary from the shape of an average jaw. Referring to FIG. 5, profile D corresponds to the shape of an average jaw. Profile E illustrates the profile of a jaw wherein the dental system has a "box-like" configuration. Profile F is illustrative of a "boat-like" dental system. The apparatus of the invention enables a sharp picture which is evenly exposed from edge to edge to be obtained of the jaw profiles illustrated in FIGS. 4 and 5 through suitable selection and variation of the speeds of motors 21 and 31.

For example, sharp photographs of the jaw profiles shown in FIGS. 4 and 5 are obtained by changing the relative speeds of the rotary motion motor 31 and the film transport motor 21 in accordance with equations determined by the mechanical motion paths. In particular, for each point on the motion path, the speeds of motors 21 and 31 must be in a certain relationship in order that the desired layer of the jaw can be sharply photographed on film RF. The appropriate speed relationships are determined from the following relationship.

$$v_f = 1 \times r_0 / [(1 - r_f + r_0) \times r_d] \times v_d$$

where
- $v_f$ = film transport speed
- $v_d$ = drive speed of rotary motion
- $l$ = distance from the focus to the film plane
- $r_0$ = distance of the layer being photographed from the instantaneous center of rotation
- $r_f$ = distance of the film plane from the instantaneous center of rotation
- $r_d$ = distance of the rotation drive point from the instantaneous center of rotation If the speed ratio $v_f/v_d$ is changed by correction of the speed of the film cartridge 20, the location of the layer being photographed as well as the exposure time will also vary. If the ratio is changed by varying the speed of the rotary motion motor 31, the location of the layer being photographed will also change. However, the exposure time will remain constant in this case as the film RF moves at a constant speed across the X-ray beam. However, it is seen from the above equation that if the speeds $v_f$ and $v_d$ of motors 21 and 31 are changed in the same proportion, the layer of the jaw that is being sharply photographed will not change in position. However, the exposure time will change.

Referring to FIG. 6, the variation in the speeds of the rotary motion motor 31 and the film transport motor 21 for one mechanical embodiment during an exposure sequence $t_0$ is illustrated. In particular, curve G shows the variation of the drive speed $v_d$ as a function of time t during the exposure sequence $t_0$. Similarly, curve H shows the variation of the drive speed $v_f$ of the transport motor 21 of film cartridge 20 as a function of time t during the exposure sequence $t_0$. Referring to curve H—$H_0$—H, the drive speed $v_f$ of the transport motor 21 of the film RF remains substantially constant during the entire exposure sequence $t_0$. Corrections for variations in the shape and/or size of the jaw to sharply focus layers whose positions differ from the standard are carried out by varying the drive speed $v_d$ of the rotary motion motor 31 so that the exposure time will be constant over the entire area of film RF. However, when photographing the front part of the dental arch it is necessary to pass the X-ray beam through the cervical spine. In this case, the exposure time which would be appropriate to other areas of the dental arch will not be appropriate for the front part of the dental arch and must be increased in this local region. The sections $G_1$ and $H_1$ in the mid-regions of curves G and H illustrate how the drive speeds $v_d$ and $v_f$ are lowered in these regions in order to increase the exposure time. The reduction in speeds $v_d$ and $v_f$ are, however, in constant mutual relationship in order to maintain the layer which is being photographed in sharp focus. Curves G and H are symmetrical with respect to the center line KK.

In addition to effecting an independent control of the speeds of the motors 21 and 31, to obtain sharp photographs at a constant exposure time of a jaw profile of almost any shape or size, the control system 100 will, preferably, also at the same time control the X-ray generator 40. As noted above, it is desired to carry out the normal X-ray photography at constant voltages and constant currents of the X-ray generator 40. The invention makes it possible to also photograph desired areas at different anode voltages if required, for example, for improving the contrast of the photograph. It is also possible to omit certain areas of the dental arch altogether from the X-ray photograph through suitable control of the X-ray generator 40. In all cases the exposure time can be maintained constant by changing the speeds $v_d$ and $v_f$ of motors 21 and 31 even though the anode voltage of the X-ray tube is changed during the exposure sequence $t_0$.

One example of the variation of the anode voltages of the X-ray tube is illustrated in FIG. 7. In this case, a photograph is required only of both condyles and also of the front teeth. In order to minimize the radiation load on the patient, the cheek areas need not be photographed and the radiation in these areas may be eliminated altogether. In FIG. 7, the curve $U_1$ illustrates the anode voltage applied to the X-ray tube. Through suitable control from keyboard 102, the voltage is reduced to zero after passing the condyle area. Similarly, the curve $U_2$ depicts the anode voltage as the X-ray beam passes the front area of the dental arch. The anode voltage is again reduced to zero during the portion of the sequence when the cheek area would have been photographed. The anode voltage is then applied again (curve $U_3$) as the X-ray tube passes over the next condyle area. During normal photography, the anode voltage will remain constant during the entire exposure, i.e., at voltage $U_0$.

In order to maintain the radiation load on the patient as low as possible, it is not always necessary to photograph the patient over the entire height of the film. For this purpose, a control system incorporated in X-ray apparatus in accordance with the invention may be coupled to the primary blind in a manner such that the shape of the radiation beam can be adjusted, e.g., by horizontally cropping off part of the radiation beam. By combining this feature with horizontal outlining of the image field as described above, only very small square regions of the jaw layer of the patient may be photographed. For example, it may be desired to obtain photographs of only the salivary glands or maxilliary sinuses. In such cases, the radiation load on the patient can be reduced to about 20% of normal full-sized panoramic X-ray photographs. This is particularly significant when the patient must attend long term, regular observations, i.e., where the permitted radiation load dose is in danger of being exceeded. Similarly, when photographing layers of the jaw of a child, the top section of the radiation beam can be cropped off with a separate primary blind thereby eliminating unnecessary radiation in the brain area.

The ability to automatically control the primary blind is not available in conventional X-ray apparatus. When such automatic control is carried out in accordance with the invention, especially when combined with the other features of the control system of the invention, optimum control of the radiation exposure can be obtained.

An automatically variable primary blind can be obtained by positioning adjacent to the tube head 10 in the path of the radiation beam X a board 15 (FIGS. 2, 8–10) formed of material which is opaque to radiation. In one embodiment (FIGS. 9 and 10) several openings of various shapes corresponding to alternative desired shapes of the radiation beam X are formed in the board 15. In another embodiment (FIG. 8) the shape of the opening in board 15 can be changed. In the case of the first embodiment, the board 15 is moved by a motor so that an opening having the desired shape will be positioned in the path of the radiation beam. In the second embodiment, the shape of the opening is changed by moving radiation-obstructing plates forming the edges of the opening by means of a motor or motors.

Figure 9:
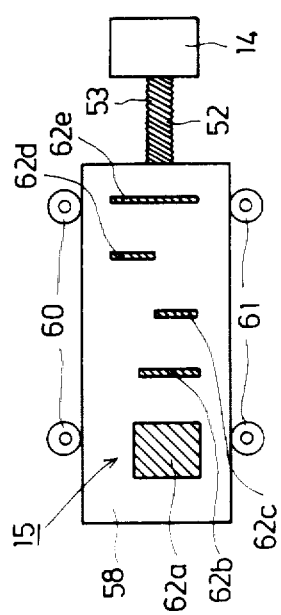
FIG. 9 is another embodiment of an adjustable primary blind.
Figure 10:
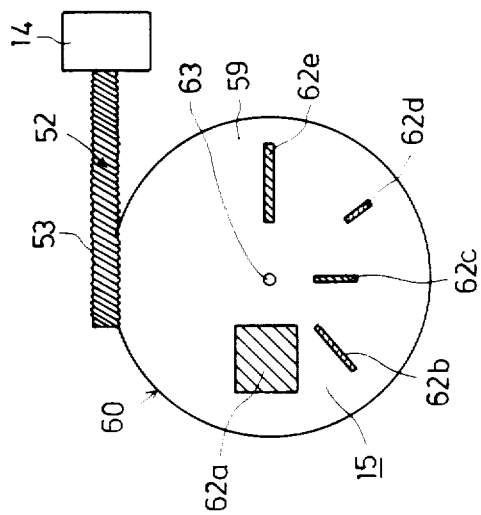
FIG. 10 is a third embodiment of an adjustable primary blind.
Figure 8:
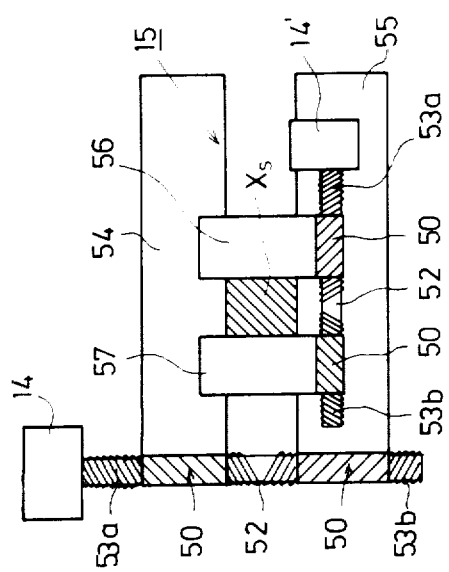
FIG. 8 is a schematic illustration showing one embodiment of an adjustable primary blind which can be controlled by a control system forming part of the X-ray apparatus of the present invention.

Referring in particular to FIGS. 8–10, the motors for the primary blind 15 are designated 14 and 14'. The motors are controlled by the control system 100 in accordance with the invention. Referring to FIG. 8, the blind 15 comprises two motors 14 and 14' which drive respective screws 52 which extend substantially perpendicularly to each other. Oppositely threaded sections 53a and 53b are provided on each of the screws 52 to which the blind board 54, 55 and 56, 57 are engaged by means of a threaded part 50, the edges of the board defining the beam opening $X_s$. Referring to FIG. 9, the motor 14 drives a screw 52 provided with threads 53 which moves the blind board 58. The blind board 58 is supported by rollers 60 and 61 so as to be movable in the horizontal direction. A set of blind openings 62a–62e are formed in board 58. A selected one of the openings 62 are moved into the path of the radiation beam X to adjust the shape of the beam. Referring to FIG. 10, the blind board 59 is circular and is mounted at its center so as to be rotatable about a shaft 63. The board 59 is provided with teeth 60 on its outer perimeters which are engaged by the thread 53 of the screw 52 which is driven by motor 15. By rotating the blind board 59 around shaft 63 under the control of control system 100, a selected one of the blind openings 62a–62e may be positioned in the path of the radiation beam X.

In some conventional panoramic tomography X-ray apparatus, an option is provided for taking cephalostatic pictures. However, this is usually found to be inconvenient and generally requires special skills for the operator, such as turning the tube head and/or manual changing of the primary blind. In some apparatus, a separate tube head with a blind is provided which renders the apparatus relatively expensive and complicated.

Figure 11:
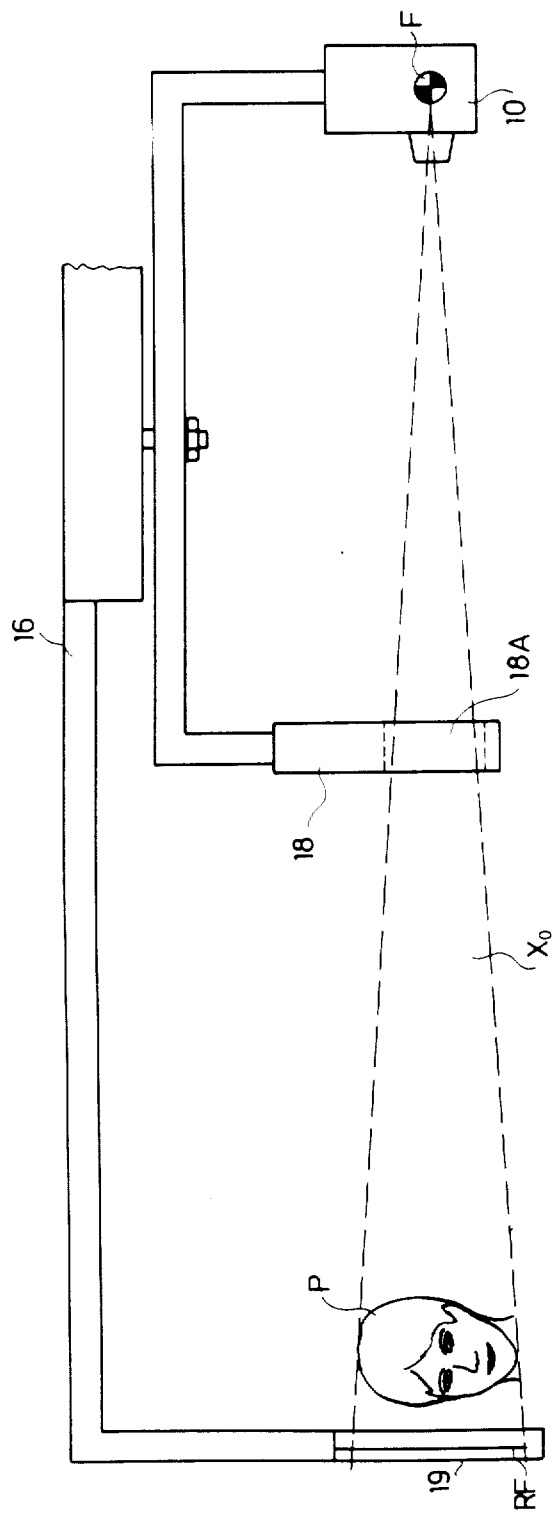
FIG. 11 is a schematic illustration of X-ray apparatus incorporating a control system in accordance with the invention for taking cephalostatic photographs.

By using X-ray apparatus incorporating a control system 100 in accordance with the invention, cephalostatic pictures may be easily obtained in a simple operation by inputting appropriate control commands at the keyboard 102. Referring to FIG. 11, the principle of utilization of the X-ray apparatus of the present invention for cephalostatic X-ray photography is illustrated. In the embodiment of FIG. 11, the control system 100 precisely controls the speeds of motors 21 and 31 and generator 40 (not shown) in the same manner as described above. However, the operation is carried out by substituting a primary blind which is suitable for cephalostatic photography for the conventional primary blind. The arm carrying the tube head 10 and the film cartridge holder 20 is driven to a position with respect to the fixed frame that the direction of the tube head 10 is correct with respect to the suspension carrying the cephalostat. The film cartridge 20 and associated equipment are moved by transport motor 21 to a position where the X-ray beam $X_0$ freely passes through an opening 18A formed in a cartridge head 18 through the patient P onto the X-ray film RF contained within the cartridge 19 fastened to the cephalostat. Since the control system 100 completely controls the X-ray generator 40, the exposure can be carried out at the desired voltage, current and time values. It is therefore seen that the control system 100 provides the X-ray apparatus with the ability to function to obtain cephalostatic photographs and it is only necessary to add a cephalostat to the panoramic tomography X-ray apparatus.

Obviously, numerous modifications and variations of the present invention are possible in the light of the above teachings. It is therefore to be understood that within the scope of the claims appended hereto, the invention may be practiced otherwise than as specifically described herein.

What is claimed is:

1. Panoramic tomography X-ray apparatus, such as for obtaining images of a dental system, comprising:
    an arm mounted for rotation;
    means for rotating said arm including a rotary motion motor;
    an X-ray generator having an X-ray tube with a tube head, said tube head being mounted on said arm for rotation therewith;
    a cartridge containing X-ray film mounted on said arm for rotation therewith;
    means for transporting said X-ray film including a film transport motor, said film transport means being mounted on said arm for rotation therewith;
    control system means for controlling the speed of said rotary motion motor of said arm, the speed of said film transport motor and the distribution of said speeds during an exposure sequence independently of each other as a function of control data and a working program in said control system means, so that dental systems of varying sizes and shapes can be photographed by said panoramic tomography X-ray apparatus both sharply and within a suitable exposure time; and
    said control system means adjusting the speed of said rotary motion motor and maintaining the speed of said film transport motor substantially constant, so that location of a layer being photographed is changed relative to the speed variations of the rotary motion motor.

2. The combination of claim 1 wherein said X-ray tube operates with an anode current and an anode voltage, and wherein in addition to comprising means for controlling the speeds of said rotary motion and film transport motors, said control system means also comprise means for controlling one of said anode current and anode voltage of said X-ray tube.

3. The combination of claim 1 further including primary blind means associated with said tube head of said X-ray generator for adjusting the shape of a radiation beam generated by said tube head.

4. The combination of claim 3 wherein said primary blind means include means for defining an aperture situated in a path of said radiation beam and means for adjusting the size and shape of said aperture, and wherein in addition to comprising means for controlling the speeds of said rotary motion and film transport motors, said control system means also comprises means for controlling said aperture adjusting means of said primary blind means to control the size and shape of said aperture thereof.

5. The combination of claim 3 wherein said primary blind means include means for defining a plurality of apertures having differing sizes and shapes and means for positioning a selected one of said apertures in a path of said radiation beam, and wherein in addition to comprising means for controlling the speeds of said rotary motion and film transport motors, said control system means also comprises means for controlling said aperture positioning means of said primary blind means to control the selection of the aperture situated in the path of said radiation beam.

6. The combination of claim 1 wherein said control system means comprise:
- a microprocessor including a program memory in which said program is pre-stored and a working memory in which said control data is stored;
- a bus coupled to said microprocessor;
- input means coupled to said bus for controlling said system;
- output means coupled to said bus and rotary and film transport motors for inter-coupling said rotary motion and film transport motors and said microprocessor so that the direction of rotation of said motors and speed distribution of said motors are controlled by said microprocessor.

7. The combination of claim 6 further including primary blind means associated with said tube head of said X-ray generator for adjusting the shape of a radiation beam generated by said tube head, said primary blind means including primary blind motor means for operating said primary blind means, and wherein said output means of said control system means are coupled to said primary blind motor means for inter-coupling said primary blind motor means and said microprocessor so that the adjustment of the shape of said radiation beam is controlled by said microprocessor.

8. The combination of claim 6 wherein said output means of said control system means are coupled to said X-ray generator for inter-coupling said X-ray generator and said microprocessor so that the X-ray generator is controlled by said microprocessor.

9. The combination of claim 8 wherein said control system means further include means coupling said tube head of said X-ray generator and microprocessor for carrying status information from tube head to said microprocessor.

10. The combination of claim 1 wherein said control system means are programmed to control both the speed distribution of said rotary motion motor of said arm and the speed distribution of said film transport motor independently of each other so that chin profiles of substantially any shape or size can be photographed with a constant exposure under the control system means.

11. The combination of claim 1 wherein said X-ray tube of said X-ray generator operates with an anode current and an anode voltage, and wherein means are provided for carrying out said photography of a dental system with both a constant anode current and a constant anode voltage of said X-ray generator.

12. The combination of claim 1 wherein said X-ray tube of said X-ray generator operates with an anode current and an anode voltage, and wherein said control system means also comprise means for controlling the anode voltage of said X-ray tube to photograph only a limited area of the dental system so that areas outside of said limited area will not be photographed in order to minimize the radiation to which a patient is subjected.

13. The combination of claim 1 further including primary blind means associated with said tube head of said X-ray generator for adjusting the shape of a radiation beam generated by said tube head, and wherein said control system means are coupled to said primary blind means so that in order to minimize the radiation load to which the patient is subjected and wherein there is no need to photograph the patient over the full height of the picture, the primary blind means are controlled by the control system means to eliminate unnecessary portions of the X-ray beam in the horizontal direction.

14. The combination of claim 1 wherein said control system means are pre-programmed to cause said X-ray apparatus to photograph only selected areas of the patient, including regions of the salivary glands and maxillary sinuses.

15. The combination of claim 1 wherein said X-ray tube of said X-ray apparatus operates with an anode current and an anode voltage, and wherein said control system means also comprise means for controlling the anode voltage, the anode current and the exposure time of said X-ray tube for obtaining cephalostatic photographs.

16. The combination of claim 15 wherein said control system means also comprise means for adjusting said tube head so as to direct a X-ray beam to a correct position of a cephalostatic patient for obtaining the cephalostatic photographs.

17. The combination of claim 15 further including primary blind means associated with said tube head of said X-ray generator for adjusting the shape of a radiation beam generated by said tube head, and wherein said control system means are coupled to said primary blind means for adjustment of the shape of the radiation beam in accordance with the requirements of cephalostatic photography.

18. The combination of claim 1, wherein said control system means control the distribution of said speeds according to the formula $$v_f = l r_o / ((l - r_f + r_o) r_d) v_d,$$

wherein
- $v_f$ = the film transport motor speed,
- $v_d$ = the rotary motion motor speed,
- $l$ = distance from a focal point of said X-ray tube to a plane of said X-ray film,
- $r_o$ = distance of the layer being photographed from an instantaneous center of rotation of said rotatable arm,
- $r_f$ = distance from the film plane to the instantaneous center of rotation, and
- $r_d$ = distance from a rotation drive point to the instantaneous center of rotation.

19. The combination of claim 1, wherein said control system means additionally control exposure time to remain constant.

20. The combination of claim 18, wherein said control system means additionally adjust said speeds in the same proportion,
whereby the exposure time changes and the location of the layer being photographed remains constant.

21. The combination of claim 5, wherein said defining means comprise a blind board with said apertures formed therethrough,
said position control means comprise a motor, and
said positioning means comprise a threaded screw coupled to said position control motor and to said blind board, and
a set of rollers upon which said blind board is supported for substantially horizontal movement.

22. The combination of claim 5, wherein said defining means comprise a substantially circular blind board with said apertures formed therethrough,
said position control means comprise a motor, and
said positioning means comprise a shaft upon which said blind board is rotatably mounted, teeth provided on an outer circumference of said blind board, and a threaded screw coupled to said positioning control motor and engaged with said teeth.

23. The combination of claim 4, wherein said aperature adjusting means comprise four blind boards, the edges of which define said aperature, and two threaded screws, each screw comprising two oppositely-threaded sections, with each of said blind boards threadingly engaged with a respective section, and said positioning control means comprise two motors, each motor coupled to a respective screw.

24. The combination of claim 16, wherein said tube head adjusting means comprise means for rotating said tube head.

* * * * *